United States Patent
Kuth

(10) Patent No.: US 7,563,233 B2
(45) Date of Patent: Jul. 21, 2009

(54) HAPTIC FEEDBACK METHOD AND APPARATUS FOR TISSUE ELASTICITY AND A VIRTUAL BOUNDARY SURFACE

(75) Inventor: Rainer Kuth, Herzogenaurach (DE)

(73) Assignee: Siemens Aktiengesellschaft, Munich (DE)

( * ) Notice: Subject to any disclaimer, the term of this patent is extended or adjusted under 35 U.S.C. 154(b) by 1577 days.

(21) Appl. No.: 10/213,040

(22) Filed: Aug. 6, 2002

(65) Prior Publication Data

US 2003/0036714 A1 Feb. 20, 2003

(30) Foreign Application Priority Data

Aug. 6, 2001 (DE) .............................. 101 38 537

(51) Int. Cl.
*A61B 5/103* (2006.01)
*A61B 5/117* (2006.01)

(52) U.S. Cl. ..................................... 600/587
(58) Field of Classification Search ................ 600/587, 600/408, 438, 442
See application file for complete search history.

(56) References Cited

U.S. PATENT DOCUMENTS

| | | | |
|---|---|---|---|
| 3,742,935 A | | 7/1973 | Baessler et al. |
| 3,919,691 A | * | 11/1975 | Noll ............................ 345/419 |
| 5,071,581 A | * | 12/1991 | Cipriano ....................... 252/77 |
| 5,339,799 A | * | 8/1994 | Kami et al. .................. 600/117 |
| 5,351,677 A | | 10/1994 | Kami et al. |
| 5,592,085 A | * | 1/1997 | Ehman ........................ 324/309 |
| 5,734,373 A | * | 3/1998 | Rosenberg et al. ........... 345/161 |
| 5,766,016 A | * | 6/1998 | Sinclair et al. ............... 434/262 |
| 5,833,633 A | * | 11/1998 | Sarvazyan .................... 600/587 |
| 5,989,199 A | * | 11/1999 | Cundari et al. .............. 600/587 |
| 6,310,604 B1 | * | 10/2001 | Furusho et al. .............. 345/156 |
| 6,491,649 B1 | * | 12/2002 | Ombrellaro ................. 600/587 |
| 6,924,787 B2 | * | 8/2005 | Kramer et al. .............. 345/156 |

FOREIGN PATENT DOCUMENTS

| | | |
|---|---|---|
| DE | PS 43 18 993 | 8/1994 |
| EP | 0 920 833 | 6/1999 |
| WO | WO 00/70362 | 11/2000 |

* cited by examiner

*Primary Examiner*—Max Hindenburg
*Assistant Examiner*—Rene Towa
(74) *Attorney, Agent, or Firm*—Schiff Hardin LLP

(57) ABSTRACT

In a method and apparatus for providing haptic feedback representing tissue elasticity, measured data based on a measurement of the elasticity of body tissue in non-contacting fashion are supplied to a machine/human interface that conveys haptic feedback information to a user dependent on the measured data. The machine/human interface enables the user to perform a relative virtual motion around a starting point in a selected tissue region. The user can thus "feel" the elasticity of tissue that is not non-invasively accessible to a touch examination from the outside. A virtual boundary of a tissue region under examination can be defined and the user, by the haptic feedback, also feels if and when this virtual boundary is reached.

14 Claims, 2 Drawing Sheets

HAPTIC FEEDBACK METHOD AND APPARATUS FOR TISSUE ELASTICITY AND A VIRTUAL BOUNDARY SURFACE

BACKGROUND OF THE INVENTION

The present invention is directed to a method for the tactile presentation of the elasticity of tissue in the inside of a body and is also directed to an apparatus for the tactile presentation of the elasticity of tissue in the inside of a body.

DESCRIPTION OF THE PRIOR ART

In the medical field, it is often significant for a diagnosis to determine the elastic behavior of tissue. It is highly advantageous to the physician for preparing a diagnosis when the elasticity of the tissue is presented to the physician not only on the basis of data but so that the physician can "feel" this elasticity, i.e. can experience the elasticity of examined tissue by means of a tactile impression.

The reason for the significance of this determination of the elasticity of tissue is that different tissue types can have different elastic properties. Particularly in the case of pathologies, the difference in the elastic properties of healthy and diseased tissue is often one of the essential distinguishing diagnostic features for the attending physician. A sensing as is known, for instance, from breast cancer screening is currently necessary in order to acquire or analyze such differences in elasticity.

It is obvious that no regions in the inside of a body can be non-invasively examined by the physician by means of direct sensing.

MR elastography and ultrasound elastography makes it possible to measure elastic properties of tissue and body parts in the inside of a body in a spatially manner resolved. MR (magnetic resonance) elastography is disclosed, for example, in PCT Application WO 00/70362. An example of ultrasound (US) elastography is presented in European Application 0 920 833.

U.S. Pat. No. 5,351,677 discloses a medical system wherein endoscopically acquired body data that reflect the surface shape and hardness of tissues are transferred into a model at which these properties can be acquired with the sense of touch.

U.S. Pat. No. 3,742,935 discloses a method in the medical field wherein a physical excursion of a sensor is amplified and simultaneously reproduced at a number of locations. A "touch platform" for tactile acquisition is thereby employed.

German PS 43 18 993 discloses an endoscopic tissue sensor that is grasped with two fingers of a hand and with which sensed reaction forces of tissue surfaces can be acquired.

On the basis of these technologies, thus, it is possible to obtain measured data that reproduce 3D resolved properties of the elasticity of deeply residing and/or very small body parts.

Moreover, various types of input devices and navigation devices for computers have been recently developed with which a force or haptic properties are returned to the user. Force return is usually referred to as force feedback, whereas the return of the haptics is referred to as tactile feedback.

SUMMARY OF THE INVENTION

It is an object of the present invention to provide a method and apparatus that enable an especially graphic, sensory presentation of the elastic properties of body tissue for the user (physician).

This object is inventively achieved in a method for the haptic presentation of the elasticity of tissue wherein a region of tissue whose elasticity is to be presented is first selected. Subsequently, the elasticity of the tissue region is measured by a non-contacting method. For example, the aforementioned US elastography or MR elastography are suitable as such a non-contacting method. Finally, the measured data are transmitted to a machine/human interface that conveys tactile feedback information dependent on the measured data to at least one finger of a user.

The machine/human interface that determines the haptic feedback information can simultaneously enable the drive of a virtual movement around a starting point in the selected tissue region.

It can be provided that a virtual section through the tissue to be examined can be selected, so that the elasticity of this virtual boundary layer is haptically presented.

The haptic feedback information can be conveyed by means of a finger receptacle that is immersed into a medium whose viscosity is controlled dependent on the measured data.

A restoring force relative to a movement of the finger receptacle in the medium can be generated dependent on the measured data.

Alternatively, the haptic feedback information can be conveyed with a planar membrane. The deformation behavior of the membrane can be set dependent on the measured elasticity data.

For example, the deformation behavior of the membrane can be set by underlying pins that are oriented essentially perpendicular to the surface of the membrane.

A capture algorithm can limit the navigation to a (virtual) boundary surface of the tissue, so that the examination automatically follows the course of the boundary surface.

According to a further aspect of the present invention, an apparatus is provided for the haptic presentation of the elasticity of tissue in the inside of a body. The apparatus has an interface for supplying data that reflect the elasticity of a tissue. The apparatus also includes arrangement for conveying haptic feedback information that is fashioned to transmit sensory impressions to the finger of a user.

The apparatus also has an interface in order to provide output information for the drive of a virtual navigation around a starting point (in the tissue under examination).

The arrangement for conveying haptic feedback information can have a finger receptacle immersed in a medium having controllable viscosity.

Alternatively, an arrangement can be provided that generates a restoring force relative to a movement of the finger receptacle in the medium.

The arrangement for conveying haptic feedback information can have a planar membrane whose deformation behavior can be set.

The deformation behavior of the membrane can be adjustable, for example, by means of underlying pins oriented essentially perpendicular to the surface of the membrane.

The apparatus can be coupled to an apparatus for the output of virtual navigation information.

DESCRIPTION OF THE PREFERRED EMBODIMENTS

Figure 1:
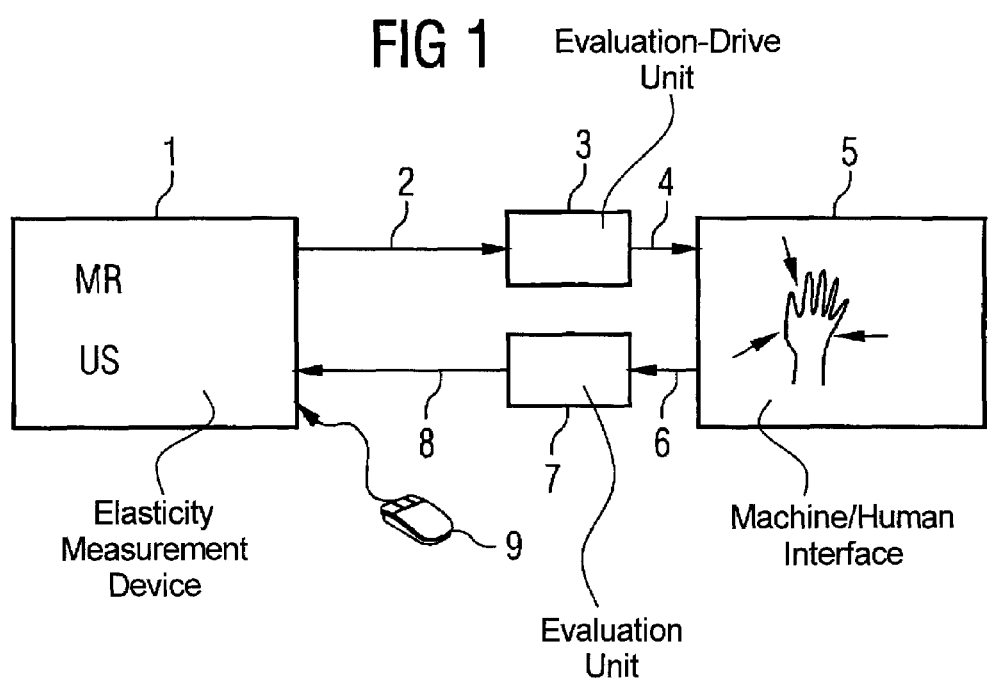
FIG. 1 is a schematic block diagram of an inventive system.

The basic component parts of an embodiment of the present invention are explained first proceeding from FIG. 1.

An elasticity measurement device measures the elasticity of tissue in a topically resolved and in non-contacting fashion. As initially stated, an MR elastograph or a US elastograph can be employed as such a device. Such a device 1 communicates measured elasticity data 2 to an evaluation-drive unit 3. This evaluation-drive unit 3 forwards drive data 4 to a machine/human interface 5 that can generally convey haptic feedback information to the user and, more specifically, to a finger of the user dependent on the drive data 4 derived from the elasticity data 2 interface.

In addition to this communication of feedback information, the interface 5 can provide virtual navigation drive data 6 to an evaluation unit 7. Dependent on a manipulation of the interface 5 with the hand or finger of a user, the evaluation unit 7 causes the measurement device 1 to modify the measurement region by means of corresponding control data 8, so that the measurement and the presentation of the elasticity can ensue in conformity with the user's wishes.

In addition or as an alternative to navigation by means of the machine/human interface 5, of course, an additional navigation drive device such as, for example, a mouse 9 as shown in FIG. 1 can be provided with which the starting point and/or the course of the examination can be selected.

A system shown in FIG. 1 can, for example, be operated in the following way:

An attending physician first selects a target or starting point that lies in the region wherein the physician would like to analyze the mechanical properties of tissue. This will usually be a boundary layer of a tissue structure.

The physician then places a finger such as, for example, the index finger in or on the haptic machine/human interface 5.

Finally, the physician moves his/her finger at or in the interface 5 and analyzes the mechanical (elastic) properties of the tissue being examined at the moment. The interface 5 reacts to every application of force of the user's finger with an opposing force, the opposing force being dependent on the mechanical (elastic) properties of the tissue under examination. The physician thus can acquire the mechanical (elastic) properties of a hypothetically freely prepared (virtual) boundary layer.

The interface 5 thus also allows a relative virtual navigation motion around the starting space in 2D or 3D space.

Advantageously, an algorithm of the type is referred to as a capture algorithm also can be provided in the invention. This capture algorithm limits navigation to a prescribed boundary surface as soon as navigation was carried out on or in the region of such a true or virtual boundary surface. The attending physician thus can also follow surfaces having a complicated course, that can even be three-dimensionally curved, since the examination automatically follows the course of the boundary surface. When the navigation approaches a boundary surface up to a prescribed distance, the navigation can automatically "leap" onto this boundary surface.

Figure 2:
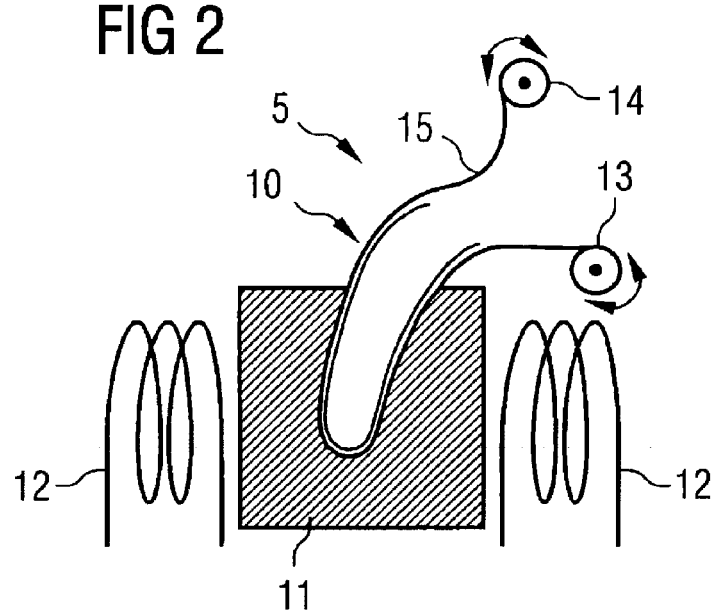
FIG. 2 illustrates a first exemplary embodiment of a machine/human interface in accordance with the invention that can convey haptic feedback information to the user dependent on measured data.

With reference to FIG. 2, a first exemplary embodiment of a machine/human interface 5 shall be explained that can convey haptic feedback information to the user dependent on measured data. According to this first exemplary embodiment, a finger receptacle 10 is provided into which, for example, the user's index finger can be inserted. The finger receptacle 10 is accepted in a container that is filled with a medium 11 having variable viscosity. For example, the viscosity can be set with coils 12 in the case of a ferro-fluid, the coils 12 generating a D-field. In this case, thus, the coils 12 are supplied with the signal 4 by the evaluation/drive unit 3 according to FIG. 1.

The finger receptacle 10 can be connected to parallel threads 15 that are conducted to braking motors 13, 14 parallel to the muscles of the finger in the finger receptacle 10. The braking power 13, 14 can likewise be controlled by a computer, namely the evaluation/drive unit 3. The combination of the variable viscosity of the medium 11 with the adjustable braking power with the braking motors 13, 14 thus makes it possible to control an opposing force relative to a movement of a finger in the finger receptacle 10 dependent on the measured data.

The brake for the threads 15 can be formed by a path sensor, a force sensor and the braking motors 13, 14, so that the brake generates a controllable opposing force.

Figure 3A:
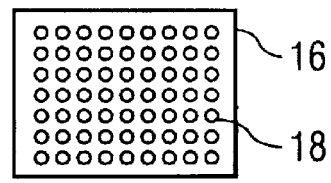
FIGS. 3a and 3b show a top view and a side view of a second exemplary embodiment of a machine/human interface in accordance with the invention for conveying haptic feedback information dependent on measured data.
Figure 3B:
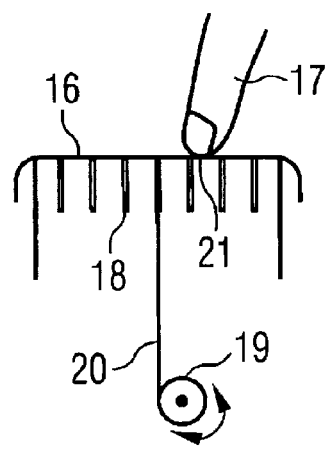

With reference to FIGS. 3a and 3b, a second exemplary embodiment of a machine/man interface 5 shall now be explained that can convey haptic feedback information to the user dependent on the measured data. According to this exemplary embodiment, the index finger 17 is placed on a membrane 16 that is essentially planar. The membrane 16 covers a matrix of pins 18 that are thus provided under the surface of the membrane 16 and are oriented perpendicularly to the surface of the membrane 16. Each pin 18 has a force sensor and path sensor as well as a braking restoring motor 19. The braking and restoring motor 19 is connected to the appertaining pin 18 with, for example, a ram or plunger 20. On the basis of the braking and restoring motors, thus, the matrix composed of the pins 18 can convey haptic feedback to the finger 17 of the operator that reflects the elasticity of the tissue at the examination location.

This exemplary embodiment has the advantages that the membrane 16 assumes the same shape, namely a slight depression, around the central contacting point 21 as given actual surface examinations by the physician.

Advantageously, such an apparatus can be installed into a known computer mouse. The operator thus can select the location at which the elasticity examination is to be performed in two dimensions with the sensing hand.

The haptic machine/human interface 5 can be part of a passive robot that allows navigation. In another exemplary embodiment, the membrane is expansive and assumes the shape of an anatomical examination region. Translational movements of the finger along the virtual section boundary thus can be acquired.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for providing a tactile presentation of tissue elasticity for tissue in an interior of a body, comprising the steps of:

in a non-contacting measurement device, electronically designating a tissue region, for which tissue elasticity is to be presented, located in an interior of a body, including designating a virtual boundary of a tissue structure in said tissue region;

measuring said elasticity of said region of said tissue with said non-contacting measurement device, and thereby obtaining measured data representing elasticity and said boundary region;

transmitting said measured data to a machine-human interface which conveys haptic feedback information to the user dependent on said measured data allowing said user to hapticly perceive said elasticity and said virtual boundary; and generating control data for said region by manipulating said machine-human interface with a finger of said user relative to said virtual boundary and using said control data to control said measurement of said elasticity.

2. A method as claimed in claim 1 comprising designating said virtual boundary by selecting a virtual section through said tissue region boundary in said virtual section.

3. A method as claimed in claim 1 comprising conveying said haptic feedback information by immersing a finger receptacle in a medium having a viscosity, and controlling said viscosity dependent on said measured data.

4. A method as claimed in claim 3 comprising generating a restoring force, relative to movement of said finger receptacle in said medium, dependent on said measured data.

5. A method as claimed in claim 1 comprising conveying said haptic feedback information by providing a planar membrane having a deformation behavior and setting said deformation behavior dependent on said measured data.

6. A method as claimed in claim 5 comprising setting said deformation behavior of said membrane by orienting a plurality of pins under said membrane substantially perpendicularly to a surface of said membrane and controlling respective forces exerted by said pins on said membrane dependent on said measured data.

7. A method as claimed in claim 1 comprising employing a navigation system to generate said control data and employing a capture algorithm to limit navigation by said navigation system to said boundary surface.

8. A system for providing a tactile presentation of elasticity of tissue located in an interior of a body, comprising:

a measurement device for non-contacting, location-dependent measurement of elasticity of tissue in a tissue region an interior of a body, said measurement device generating measurement data representing said elasticity;

an input unit allowing manual input of a virtual boundary of a tissue structure in said tissue region, and said measurement device including data, in said measurement data, representing said virtual boundary;

a machine-human interface supplied with said measurement data, and adapted to interact with a finger of a user, to convey haptic feedback information dependent on said measurement data to said finger allowing said user to perceive said elasticity and said virtual boundary; and a control data generator for generating control data dependent on manipulation of said machine-human interface with said finger relative to said virtual boundary, said control data being supplied to said measurement device and controlling acquisition of said measurement data by said measurement device.

9. A system as claimed in claim 8 wherein said machine-human interface comprises a finger receptacle immersed in a medium having a viscosity controllable dependent on said measurement data.

10. A system as claimed in claim 9 wherein said machine-human interface further comprises an arrangement which generates a restoring force relative to movement of said finger receptacle in said medium.

11. A system as claimed in claim 8 wherein said machine-human interface comprises a planar membrane having a deformation behavior settable dependent on said measurement data.

12. A system as claimed in claim 11 wherein said machine-human interface further comprises a plurality of pins underlying said membrane and oriented substantially perpendicularly to a surface of said membrane, said pins exerting respective forces on said membrane dependent on said measurement data.

13. A system as claimed in claim 8 further comprising an arrangement for generating said control data dependent on said measurement data for virtual navigation.

14. A system as claimed in claim 13 further comprising an arrangement operating on a capture algorithm that limits navigation, dependent on said navigation information, relative to a said virtual boundary.

* * * * *